United States Patent
Hamanaga et al.

(10) Patent No.: US 12,089,922 B2
(45) Date of Patent: Sep. 17, 2024

(54) MRI APPARATUS AND NON-TRANSITORY COMPUTER-READABLE STORAGE MEDIUM

(71) Applicant: CANON MEDICAL SYSTEMS CORPORATION, Otawara (JP)

(72) Inventors: Shohei Hamanaga, Nasushiobara (JP); Yuki Takai, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 3 days.

(21) Appl. No.: 18/046,997

(22) Filed: Oct. 17, 2022

(65) Prior Publication Data
US 2023/0126958 A1    Apr. 27, 2023

(30) Foreign Application Priority Data
Oct. 22, 2021 (JP) .................. 2021-173246

(51) Int. Cl.
*A61B 5/055* (2006.01)
*G01R 33/56* (2006.01)

(52) U.S. Cl.
CPC .......... *A61B 5/055* (2013.01); *G01R 33/5608* (2013.01)

(58) Field of Classification Search
CPC .................. A61B 5/055; G01R 33/5608
See application file for complete search history.

(56) References Cited

U.S. PATENT DOCUMENTS

| | | | |
|---|---|---|---|
| 5,151,656 A | 9/1992 | Maier et al. | |
| 11,119,175 B2* | 9/2021 | Gao | G01R 33/5616 |
| 2002/0000805 A1 | 1/2002 | Kuhara | |
| 2004/0245986 A1 | 12/2004 | Kumai et al. | |
| 2015/0355303 A1* | 12/2015 | Kuhara | G01R 33/5611 324/322 |
| 2019/0033407 A1* | 1/2019 | Seo | G01R 33/56545 |

FOREIGN PATENT DOCUMENTS

| | | |
|---|---|---|
| JP | 05-068674 A | 3/1993 |
| JP | 2003-116815 A | 4/2003 |
| JP | 2011-031072 A | 2/2011 |
| JP | 2013-240537 A | 12/2013 |

* cited by examiner

*Primary Examiner* — Gregory H Curran
(74) *Attorney, Agent, or Firm* — Oblon, McClelland, Maier & Neustadt, L.L.P.

(57) ABSTRACT

An MRI apparatus includes a scanner configured to apply an RF pulse to an object and processing circuitry configured to: set a first pulse sequence in which acquisition of a first set of MR signals is started after a first delay time from application of a first excitation pulse, and a second pulse sequence in which acquisition of a second set of MR signals is started after a second delay time from application of a second excitation pulse, the second delay time being different from the first delay time; acquire first and second sets of MR signals by causing the scanner to apply the first and second pulse sequences to the object; generate a combined dataset by averaging a first dataset based on the first set of MR signals and a second dataset based on the second set of MR signals; and reconstruct an MR image based on the combined dataset.

13 Claims, 13 Drawing Sheets

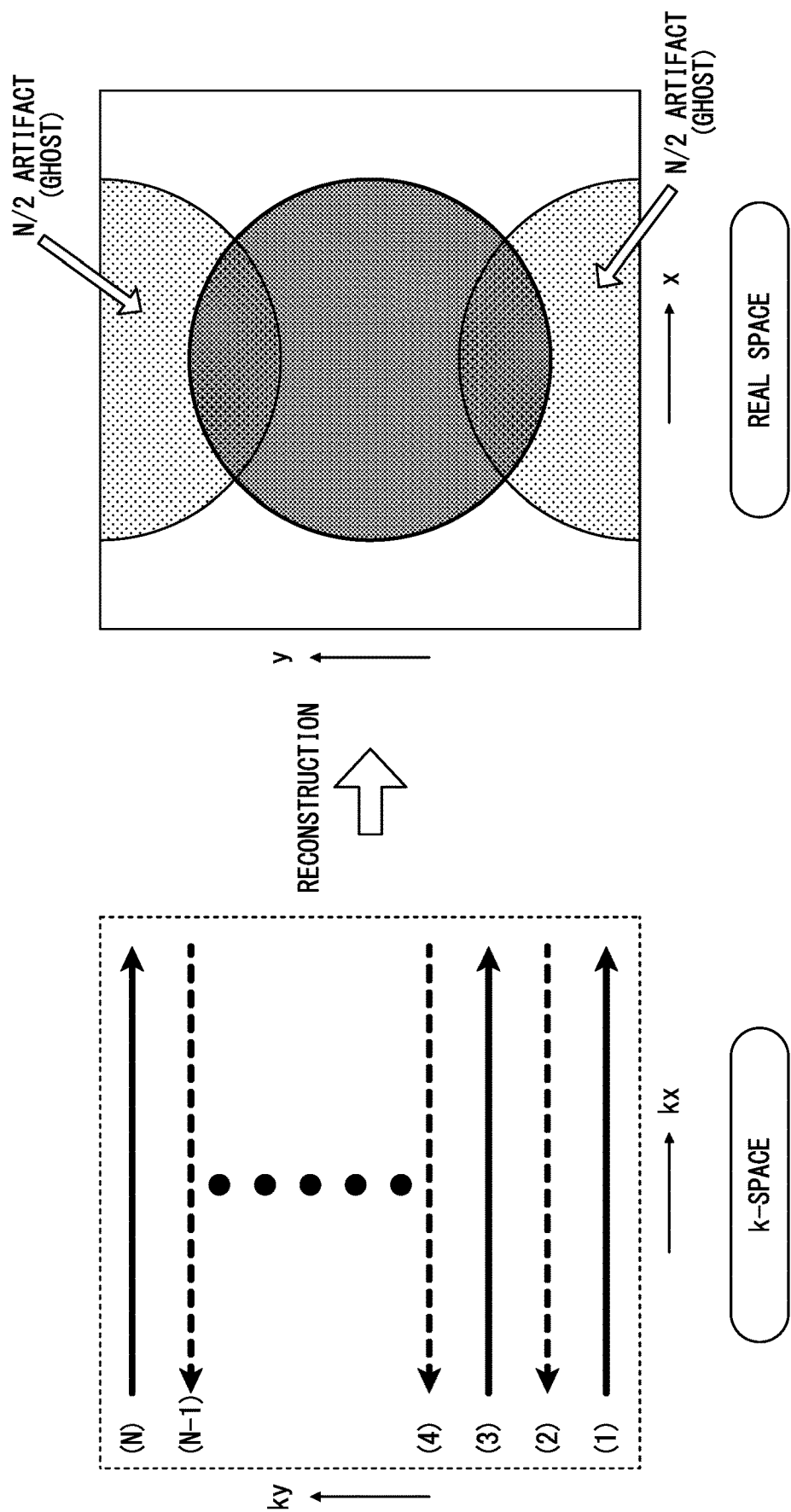

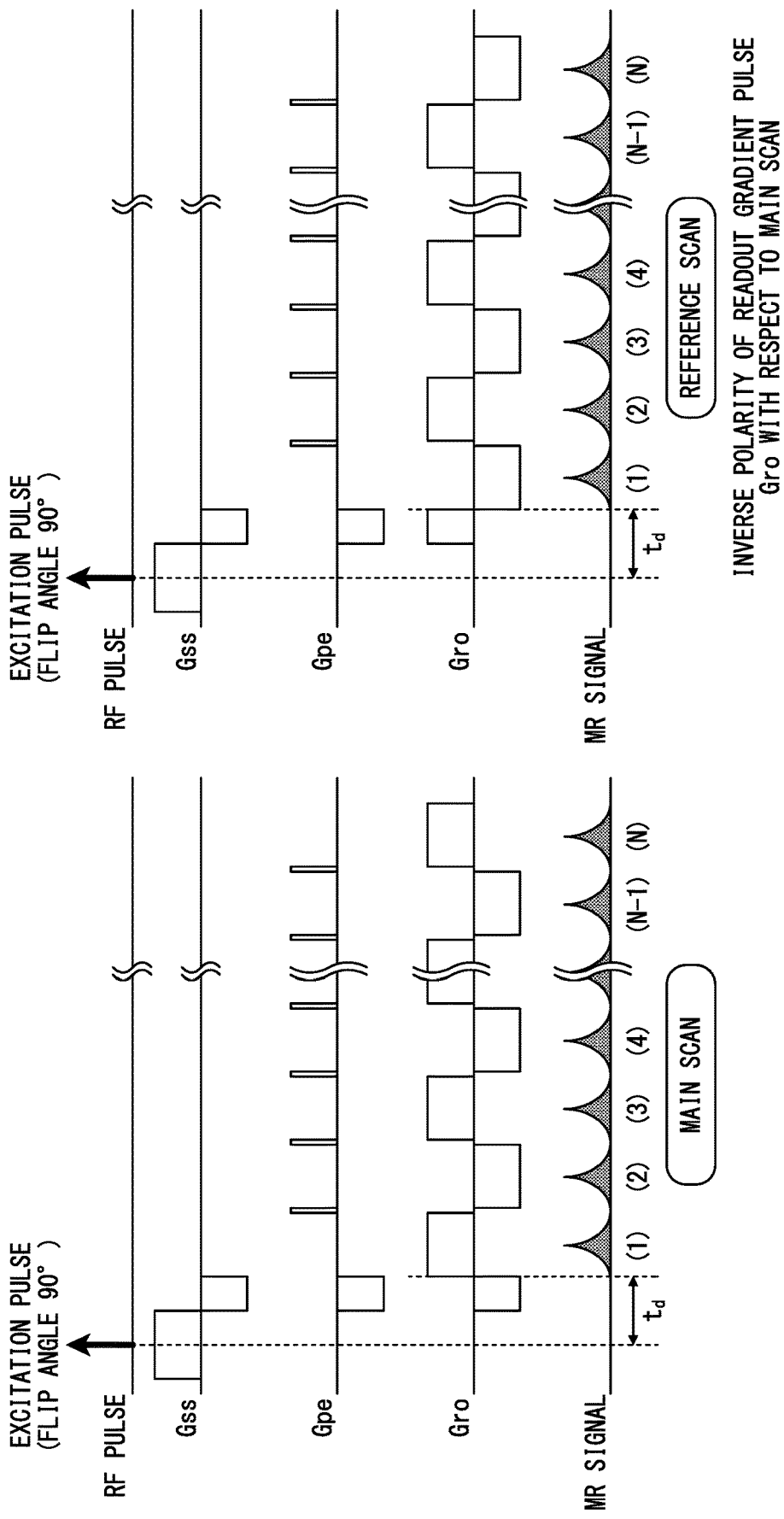

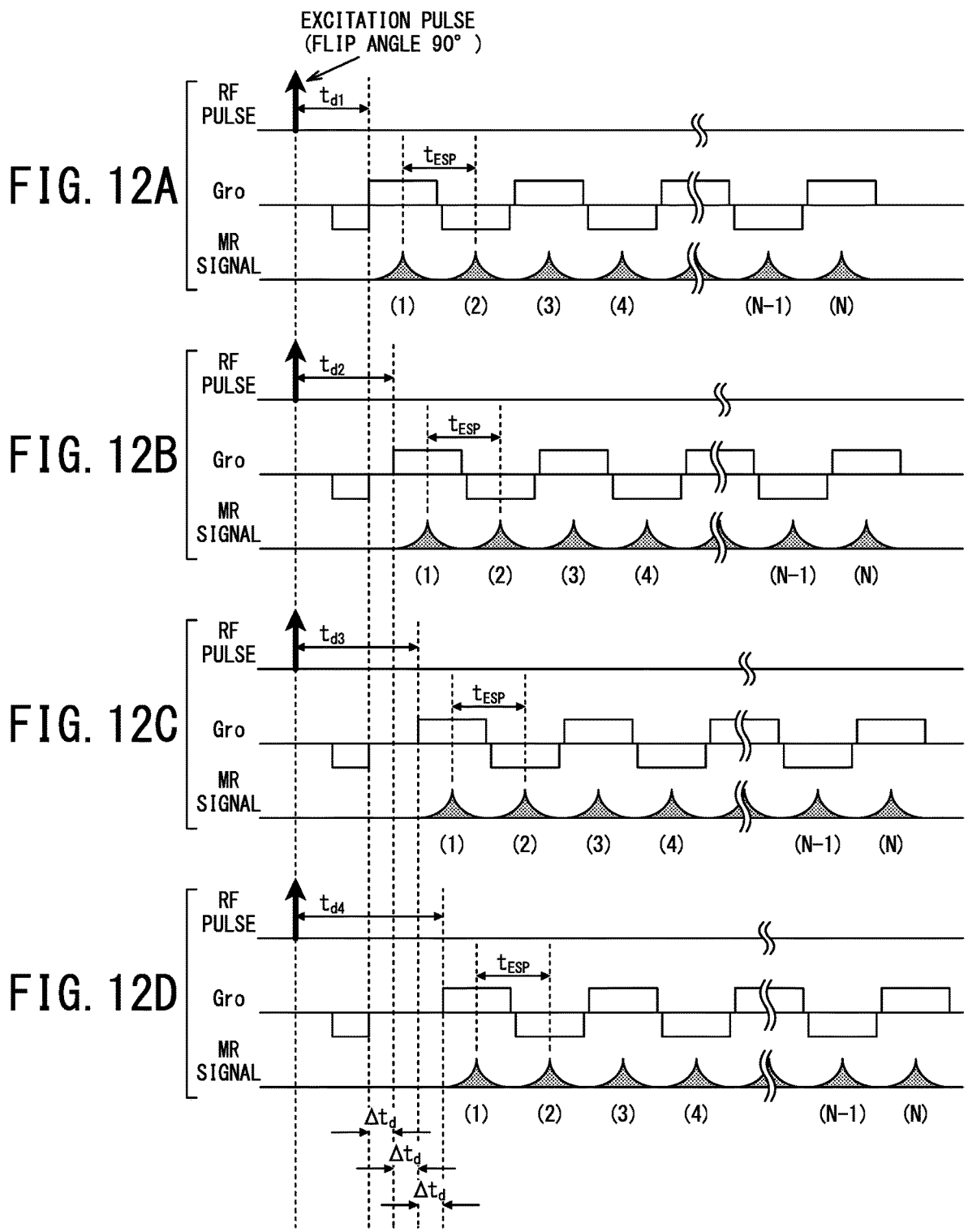

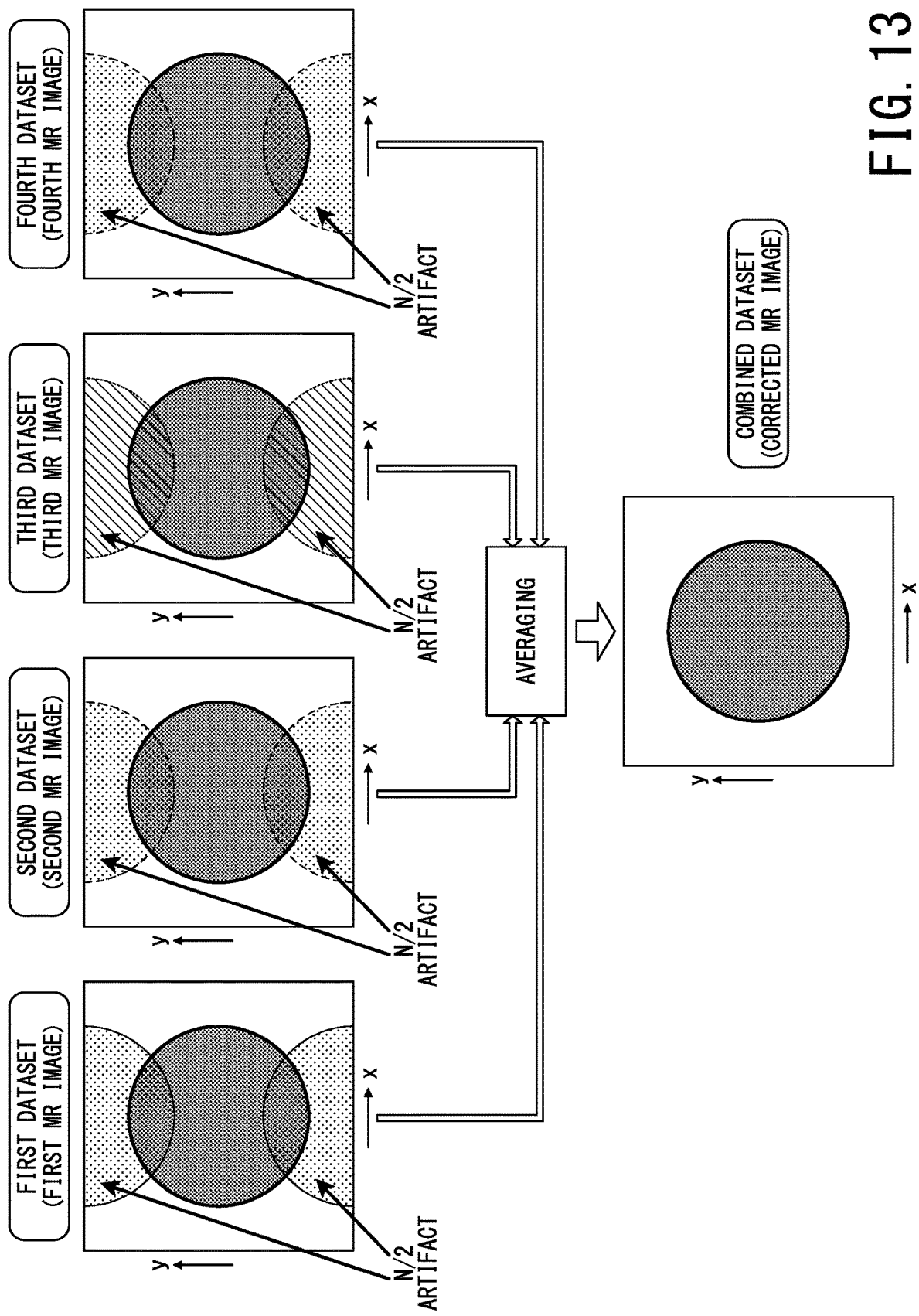

MRI APPARATUS AND NON-TRANSITORY COMPUTER-READABLE STORAGE MEDIUM

CROSS-REFERENCE TO RELATED APPLICATION

This application is based upon and claims the benefit of priority from Japanese Patent Application No. 2021-173246, filed on Oct. 22, 2021, the entire contents of which are incorporated herein by reference.

FIELD

Disclosed embodiments relate to a magnetic resonance imaging (MRI) apparatus and a non-transitory computer-readable storage medium.

BACKGROUND

An MRI apparatus is an imaging apparatus which excites nuclear spin of an object placed in a static magnetic field with a radio frequency (RF) pulse having the Larmor frequency and reconstructs an image on the basis of magnetic resonance (MR) signals emitted from the object due to the excitation.

One of the imaging techniques of MRI is a high-speed imaging method called echo planar imaging (EPI). In EPI, the MRI apparatus acquires MR signals while stepwisely adding a certain phase encoding amount and alternately inverting the polarity of the readout gradient magnetic field between positive and negative, for example.

EPI is an imaging method that enables MR signals necessary for image generation to be acquired in a very short time, but is also an imaging method that is prone to generate an artifact. For example, when MR signals are acquired for the respective phase encodes while the polarity of the readout gradient magnetic field is being alternately inverted, the phase errors included in the respective MR signals differ between MR signals of odd-numbered lines and MR signals of even-numbered lines in the phase encoding direction. As a result, it is known that an artifact called a N/2 artifact (i.e., N-half artifact or N-half ghost artifact) occurs. The N/2 artifact is a ghost of the true image that appears at a position shifted in the phase-encoding direction by, for example, ½ of the FOV (Field of View).

Although various techniques have been proposed for suppressing N/2 artifacts conventionally, it is difficult to completely remove N/2 artifacts and further improvement is desired.

BRIEF DESCRIPTION OF THE DRAWINGS

In the accompanying drawings:

FIG. 3A and FIG. 3B are schematic diagrams illustrating N/2 artifacts that occur in the EPI method;

FIG. 5A and FIG. 5B are schematic diagrams illustrating the concept of the second conventional method of suppressing N/2 artifacts;

FIG. 12A to FIG. 12D are sequence diagrams of respective four pulse sequences of the EPI method in the second embodiment; and FIG. 13 is a schematic diagram illustrating the effect of the N/2 artifact suppression processing executed by the MRI apparatus 1 according to the second embodiment.

DETAILED DESCRIPTION

Hereinafter, embodiments of the present invention will be described by referring to the accompanying drawings.

In one embodiment, an MRI apparatus includes: a scanner that includes a static magnetic field magnet configured to generate a static magnetic field, a gradient coil configured to generate a gradient magnetic field, and a whole body (WB) coil configured to apply an RF pulse to an object; and processing circuitry. This processing circuitry is configured to: set a first pulse sequence and a second pulse sequence, the first pulse sequence being a pulse sequence in which acquisition of a first set of MR signals is started after elapse of a first delay time from application of a first excitation pulse, the second pulse sequence being a pulse sequence in which acquisition of a second set of MR signals is started after elapse of a second delay time from application of a second excitation pulse, the second delay time being different from the first delay time; acquire a first set of MR signals by causing the scanner to apply the first pulse sequence to the object; acquire a second set of MR signals by causing the scanner to apply the second pulse sequence to the object; generate a combined dataset by averaging a first dataset based on the first set of MR signals and a second dataset based on the second set of MR signals; and reconstruct a magnetic resonance image based on the combined dataset.

First Embodiment

Figure 1:
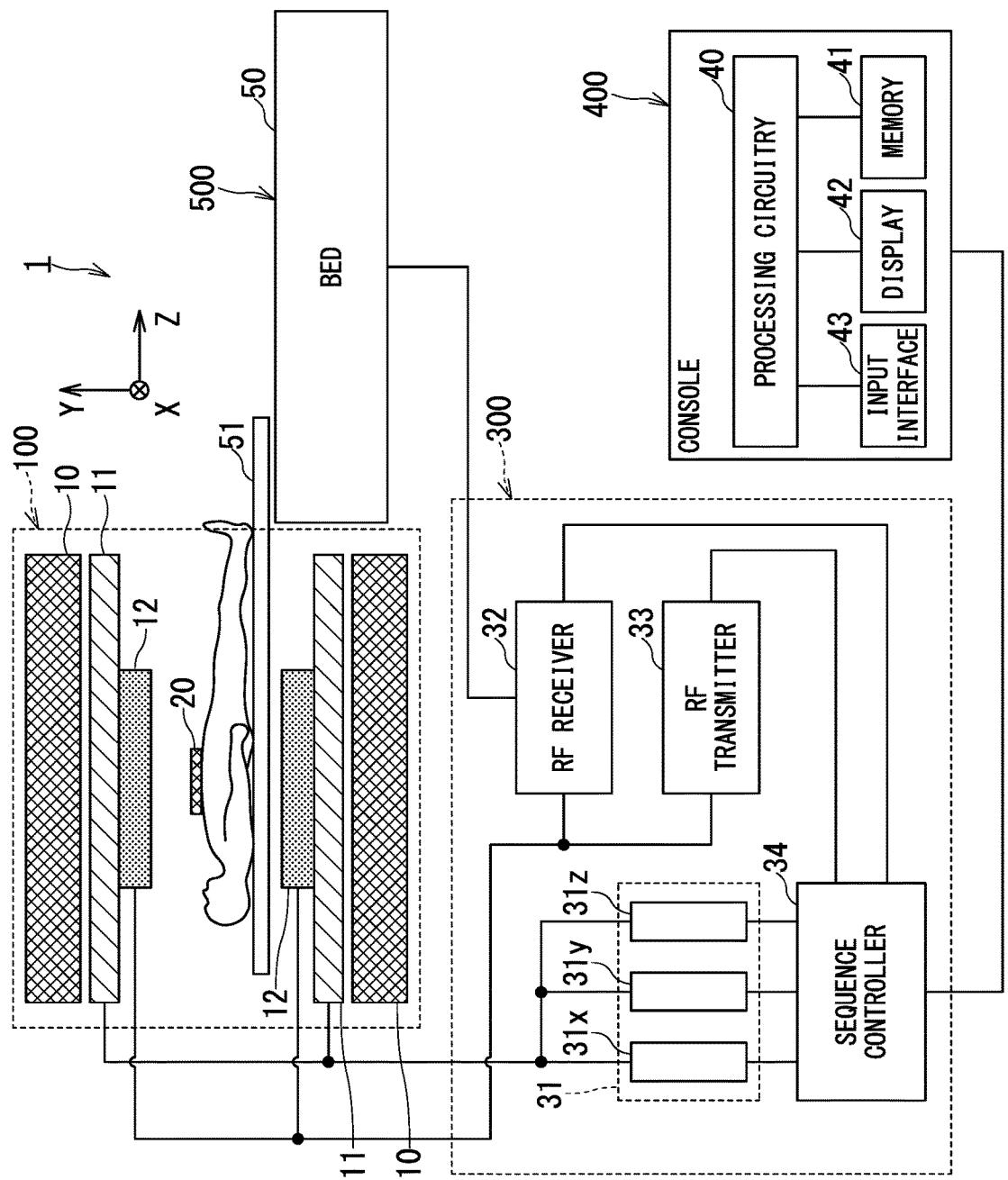
FIG. 1 is a configuration diagram illustrating an overall configuration of an MRI apparatus according to the first embodiment.

FIG. 1 is a block diagram illustrating an overall configuration of an MRI apparatus 1 according to the first embodiment. The MRI apparatus 1 according to the first embodiment includes a gantry 100, a bed 500, a control cabinet 300, and a console 400.

The gantry 100 includes a static magnetic field magnet 10, a gradient coil 11, and a whole body (WB) coil 12, and these components are housed in a cylindrical housing. The bed 500 includes a bed body 50 and a table 51. The MRI apparatus 1 includes at least one RF coil 20 (i.e., surface coil or local coil 20) to be disposed close to an object.

The control cabinet 300 includes: a static magnetic field power supply (not shown); three gradient coil power supplies 31 (31x for an X-axis, 31y for a Y-axis, and 31z for a Z-axis); an RF receiver 32; an RF transmitter 33; and a sequence controller 34.

The static magnetic field magnet 10 of the gantry 100 is substantially in the form of a cylinder and generates a static magnetic field inside a bore, which is a space inside the cylindrical structure of the static magnetic field magnet 10 and is also an imaging region of an object such as a patient. The static magnetic field magnet 10 includes a superconducting coil inside, and the superconducting coil is cooled down to an extremely low temperature by liquid helium. The static magnetic field magnet 10 generates a static magnetic field by supplying the superconducting coil with an electric current provided from the static magnetic field power supply (not shown) in an excitation mode. Afterward, the static magnetic field magnet 10 shifts to a permanent current mode, and the static magnetic field power supply is separated. Once it enters the permanent current mode, the static magnetic field magnet 10 continues to generate a strong static magnetic field for a long time, for example, over one year. Note that the static magnetic field magnet 10 may be configured as a permanent magnet.

The gradient coil 11 is also substantially in the form of a cylinder and is fixed to the inside of the static magnetic field magnet 10. This gradient coil 11 applies gradient magnetic fields to the object in the respective directions of the X-axis, the Y-axis, and the Z-axis by using electric currents supplied from the gradient coil power supplies 31x, 31y, and 31z.

The bed body 50 of the bed 500 can move the table 51 in the vertical direction and moves the table 51 with the object placed thereon to a predetermined height before imaging. Afterward, during the imaging, the bed body 50 moves the table 51 in the horizontal direction so as to move the object to the inside of the bore.

The WB coil 12 is shaped substantially in the form of a cylinder so as to surround the object and is fixed to the inside of the gradient coil 11. The WB coil 12 applies RF pulses transmitted from the RF transmitter 33 to the object, and receives MR signals emitted from the object due to excitation of hydrogen nuclei.

The RF coil 20 is also called a surface coil or a local RF coil, and receives MR signals emitted from the object at a position close to the body surface of the object. The RF coil 20 includes a plurality of coil elements, for example. There are various types of RF coils 20 depending on the body part to be imaged of the object, such as the head, the chest, the spine, the lower limbs, and the whole body. FIG. 1 illustrates the RF coil 20 for imaging the chest.

The RF transmitter 33 transmits RF pulses to the WB coil 12 based on the instruction from the sequence controller 34. The RF receiver 32 receives MR signals detected by the WB coil 12 and/or the RF coil 20, digitizes the detected MR signals, and transmits the digitized MR signals to the sequence controller 34.

The sequence controller 34 performs a scan of the object by driving the gradient coil power supplies 31, the RF transmitter 33, and the RF receiver 32 under the control of the console 400. The sequence controller 34 receives MR signals acquired through the scan from the RF receiver 32, and transmits the received MR signals to the console 400.

The sequence controller 34 includes processing circuitry (not shown). This processing circuitry is configured as a processor, which executes predetermined programs, or is configured as hardware such as a field programmable gate array (FPGA) and an application specific integrated circuit (ASIC), for example.

The console 400 is configured as a computer that includes processing circuitry 40, a memory 41, an input interface 43; and a display 42.

The memory 41 is a recording medium including a read-only memory (ROM) and/or a random-access memory (RAM) in addition to an external memory device such as a hard disk drive (HDD) and an optical disc device. The memory 41 stores various programs to be executed by the processor of the processing circuitry 40 as well as various data and information.

The input interface 43 includes various devices for an operator to input various data and information, and is configured of a mouse, a keyboard, a trackball, and/or a touch panel, for example.

The display 42 is a display device such as a liquid crystal display panel, a plasma display panel, and an organic EL panel.

The processing circuitry 40 is a circuit provided with a central processing unit (CPU) and/or a special-purpose or general-purpose processor, for example. The processor implements various functions described below by executing the programs stored in the memory 41. The processing circuitry 40 may be configured as hardware such as an FPGA and an ASIC. The various functions described below can also be implemented by such hardware. Additionally, the processing circuitry 40 can implement the various functions by combining hardware processing and software processing based on its processor and programs.

The console 400 comprehensively controls the MRI apparatus 1. Specifically, the console 400 receives various information items and instructions including imaging conditions through the input interface 43 such as a mouse and/or a keyboard that are operated by an operator such as a medical imaging technologist. The processing circuitry 40 causes the sequence controller 34 to perform a scan on the basis of the inputted imaging conditions, and reconstructs an image on the basis of raw data transmitted from the sequence controller 34. The reconstructed image is displayed on the display 42 or stored in the memory 41.

The MRI apparatus 1 according to the first embodiment enables reduction of N/2 artifacts, which occur in the EPI method, in a relatively simpler manner than the conventional techniques. Prior to describing the first embodiment, a description will be given of a typical EPI method, N/2 artifacts, and the conventional N/2 artifact suppression techniques.

Figures 2A, 2B:
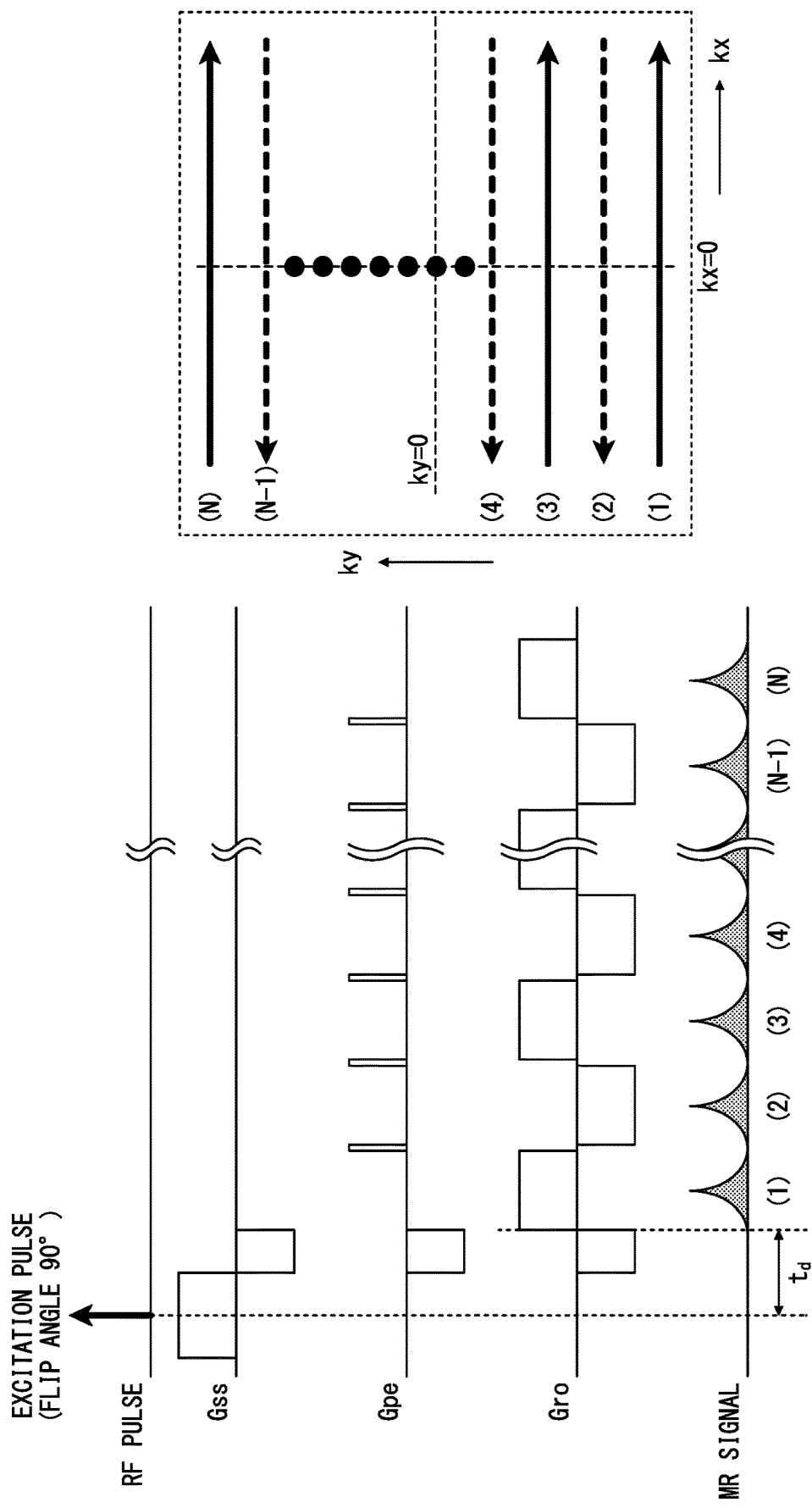
FIG. 2A is a schematic diagram illustrating a pulse sequence of a typical GRE (gradient echo)-based EPI method (GRE-EPI)
FIG. 2B is a schematic diagram illustrating how to fill k-space with the acquired data in the case of GRE-EPI shown in FIG. 2A.

FIG. 2A illustrates a pulse sequence of a typical GRE (gradient echo)-based EPI method (GRE-EPI). The first row in FIG. 2A shows the RF pulse. In the GRE-based EPI method, one excitation pulse is applied as the RF pulse. The flip angle of the excitation pulse is set to 90°, for example.

The second row in FIG. 2A shows the slice selection gradient pulse Gss. Although the application direction of the slice selection gradient pulse Gss can be any direction, in the following description, it is assumed to be the Z-axis direction (FIG. 1) corresponding to the head-foot direction of the object.

The third row in FIG. 2A shows the phase encoding gradient pulse Gpe. Although the application direction of the phase encoding gradient pulse Gpe can also be any direction, in the following description, it is assumed to be the Y-axis direction (FIG. 1) corresponding to the anterior-posterior direction of the object.

The fourth row in FIG. 2A shows the readout gradient pulse Gro. In the following description, the application direction of the readout gradient pulse Gro is assumed to be the X-axis direction (FIG. 1) corresponding to the right-left direction of the object.

In the EPI method, the readout gradient pulse Gro is repeatedly applied while being inverted into positive and negative polarity alternately, and a blip-like phase encoding gradient pulse Gpe having a short pulse width is applied between the respective readout gradient pulses Gro.

The negative phase encoding gradient pulse Gpe having wide pulse width (i.e., pre-phasing pulse), which is applied immediately after the excitation pulse, is used for bringing the initial value of the phase encode amount to the maximum value on the negative side. The negative readout gradient pulse Gro having half pulse width (i.e., pre-phasing pulse), which is applied immediately after the excitation pulse, is used for bringing the initial value of the frequency encode amount to the maximum value on the negative side.

The fifth row in FIG. 2A shows MR signals. N sets of MR signals from the repetition number (1) to the repetition number (N) are read out by the respective readout gradient pulses Gro, for example. K-space represented by kx and ky directions shown in FIG. 2B is filled with the digitized MR signals acquired by the pulse sequence of the above-described EPI method.

Filling of the k-space is performed in accordance with the application order and application direction of the phase encoding gradient pulses Gpe and the readout gradient pulses Gro. For example, in the k-space, the line (1), which correspond to the negative maximum value in the phase encoding direction (i.e., ky direction), is filled with the MR signal of the repetition number (1) along the frequency encoding direction (i.e., kx direction) from negative to positive. The line (2) of the phase encoding direction (i.e., ky direction) is filled with the MR signal of the repetition number (2) along the frequency encoding direction (i.e., kx direction) from positive to negative.

As described above, the lines (1) to (N) of the phase-encoding direction (i.e., ky direction) in the k-space are filled with the respective MR signals of the repetition numbers (1) to (N) in such a manner that the filling direction is alternately inverted for each line along the frequency encoding direction (i.e., kx direction).

In FIG. 2B, the odd-numbered lines are indicated by solid lines and the even-numbered lines are indicated by broken lines.

FIG. 3A and FIG. 3B are schematic diagrams illustrating N/2 artifacts that occur in the EPI method.

Note that FIG. 3A is a schematic diagram illustrating the k-space filled with the MR signals (i.e., k-space data) and is the same as FIG. 2B. FIG. 3B is a schematic diagram illustrating N/2 artifacts. In FIG. 3B, the central circle is the true image, and the upper and lower semicircles are N/2 artifacts, i.e., ghosts of the true image.

N/2 artifacts are due to variation in amplitude and/or phase of the MR signals between odd-numbered lines and even-numbered lines. The causes of variation in amplitude and/or phase of the MR signals between odd and even lines include various imperfections such as an eddy magnetic field and non-uniformity of the static magnetic field.

The periodic variation in amplitude and/or phase of the MR signals between the odd and even lines generates periodic variation with a period of 2/N in the phase encoding direction (i.e., ky direction) of the k-space. As a result, in the real space generated by performing Fourier transform on the k-space data, a ghost (i.e., N/2 artifact) occurs in the Y-axis direction, which corresponds to the phase encoding direction, with a period of N/2, which is the reciprocal of the period of 2/N.

N/2 artifacts appear at both positions where the true image is shifted by half the FOV (i.e., by half of the total number of lines in the Y-axis direction) in the positive or negative direction along the Y-axis direction. The appearance of N/2 artifacts are not limited to the above-described positions when parallel imaging is used in combination with EPI to thin out lines in the Y-axis direction. However, for convenience of explanation, the following description is based on the assumption that N/2 artifacts are generated at positions shifted from the true image by half of the total number N of the lines in the Y-axis direction. The N/2 artifact is a ghost image that is unnecessary for image diagnosis, and techniques for suppressing N/2 artifacts have been conventionally studied.

FIG. 4A to FIG. 5B are schematic diagrams illustrating typical conventional N/2 artifact suppression techniques.

Figures 4A, 4B:
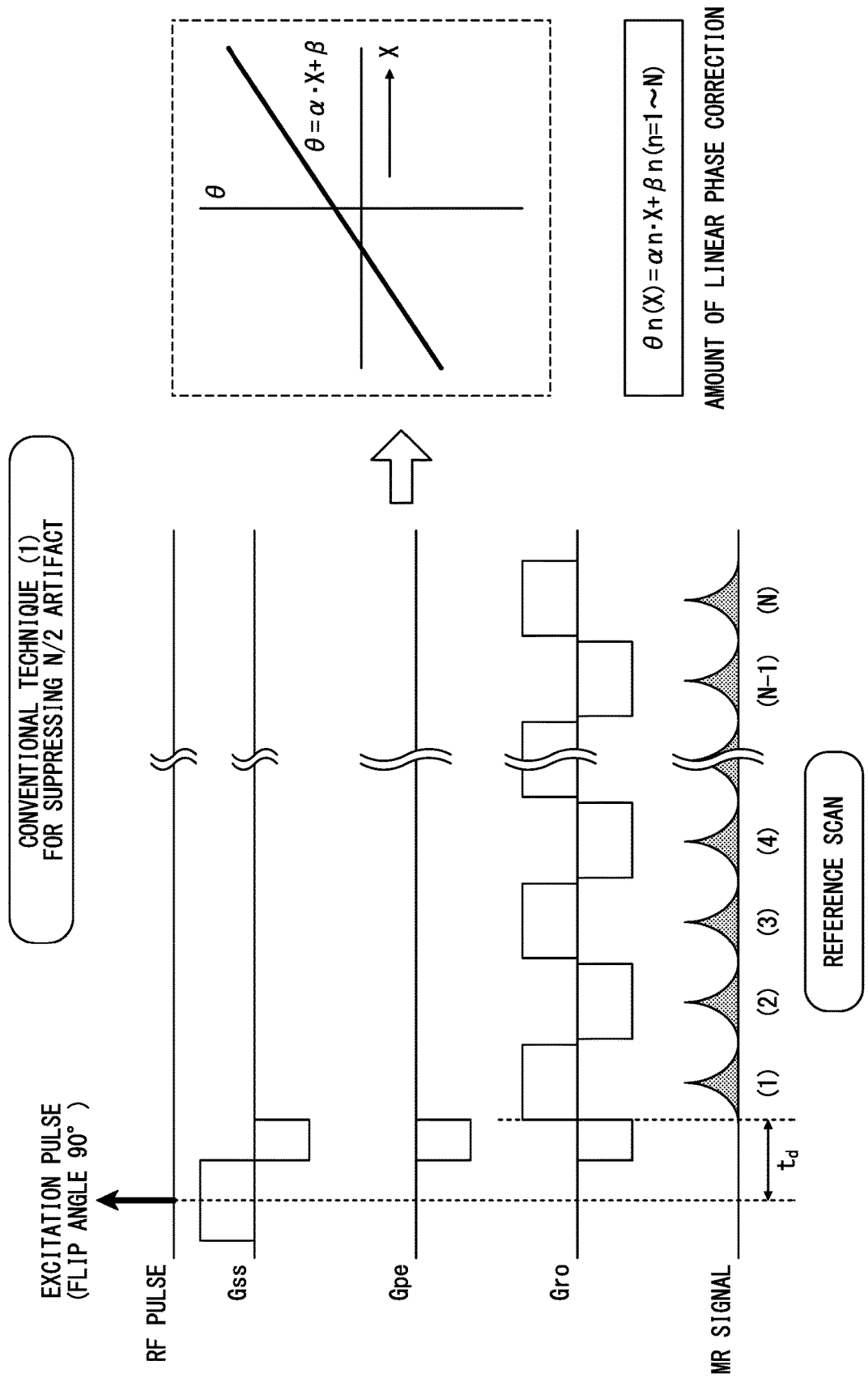
FIG. 4A and FIG. 4B are schematic diagrams illustrating the concept of the first conventional method of suppressing N/2 artifacts.

FIG. 4A and FIG. 4B are schematic diagrams illustrating the concept of the first conventional method of suppressing N/2 artifacts disclosed in, for example, JP H05-068674 A (Hereinafter, referred to as Patent Document 1). In the first conventional method, a reference scan is performed to acquire MR signals separately from a scan for generating a diagnostic image (hereinafter referred to as a main scan, or a diagnostic scan). In the first conventional method, phase correction data are generated from the MR signals acquired in the reference scan, and the data acquired in the main scan are corrected on the basis of the phase correction data.

Specifically, in the reference scan as shown in FIG. 4A, MR signals of numbers (1) to (N) are acquired by applying the same pulse sequence to the object as the main scan of the EPI method except that no phase encoding gradient pulse is applied. These MR signals are subjected to one-dimensional Fourier transform in the X-axis direction to obtain a phase amount of the complex signal at each position in the real space in the X-axis direction, which is used for calculating a linear expression of the phase error θn(X), as described below, by linear approximation using the least-square method, for example.

$$\theta n(X) = \alpha n \cdot X + \beta n (n=1 \text{ to } N) \quad \text{Expression 1}$$

N/2 artifacts are suppressed by correcting the phase of the data acquired in the main scan using the linear approximation represented by Expression 1, i.e., the linear phase correction amount.

FIG. 5A and FIG. 5B are schematic diagrams illustrating the concept of the second conventional method of suppressing N/2 artifacts disclosed in, for example, JP 2003-116815 A (Hereinafter, referred to as Patent Document 2). In the second conventional method, data acquired by the main scan and data acquired by the reference scan executed separately from the main scan are added in complex numbers, and these complex-added data are used for generating an image in the real space.

In the second conventional method, the polarity of the readout gradient pulse is opposite between the pulse sequence of the main scan (FIG. 5A) and the pulse sequence of reference scan (FIG. 5B). That is, of two MR signals added in complex numbers, one MR signal is acquired by the readout gradient pulse having positive polarity whereas the other MR signal is acquired by the readout gradient pulse having negative polarity.

In the second conventional method, complex addition of two MR signals acquired by readout gradient pulses having the opposite polarities eliminates the phase error (i.e., the phase errors are canceled by each other), resulting in suppression of N/2 artifacts.

However, in the first conventional method, the approximation of the phase error used for correction is linear, and consequently, nonlinear phase errors of second or higher order cannot be corrected. Thus, in the first conventional method, nonlinear phase errors remain, and the N/2 artifacts cannot be completely suppressed.

In the second conventional method, two data acquired by the respective readout gradient pulses having the opposite polarities (i.e., positive and negative pulses) are added in complex numbers. However, the influence of disturbance caused by, for example, an eddy current differs depending on the polarity of the readout gradient pulse. Hence, complex addition of two MR signals cannot completely eliminate the phase errors. Further, due to the opposite polarity of the readout gradient pulses, the polarity of the phase error in the readout direction is inverted, and thus, the deviation direction of the positional errors in the real space becomes opposite. Consequently, when two pixel values are added and averaged, an image blur is more likely to occur due to the averaging of pixel value.

The method for suppressing N/2 artifacts in the present embodiment solves the above-described problems in the first and second conventional methods.

Figure 6:
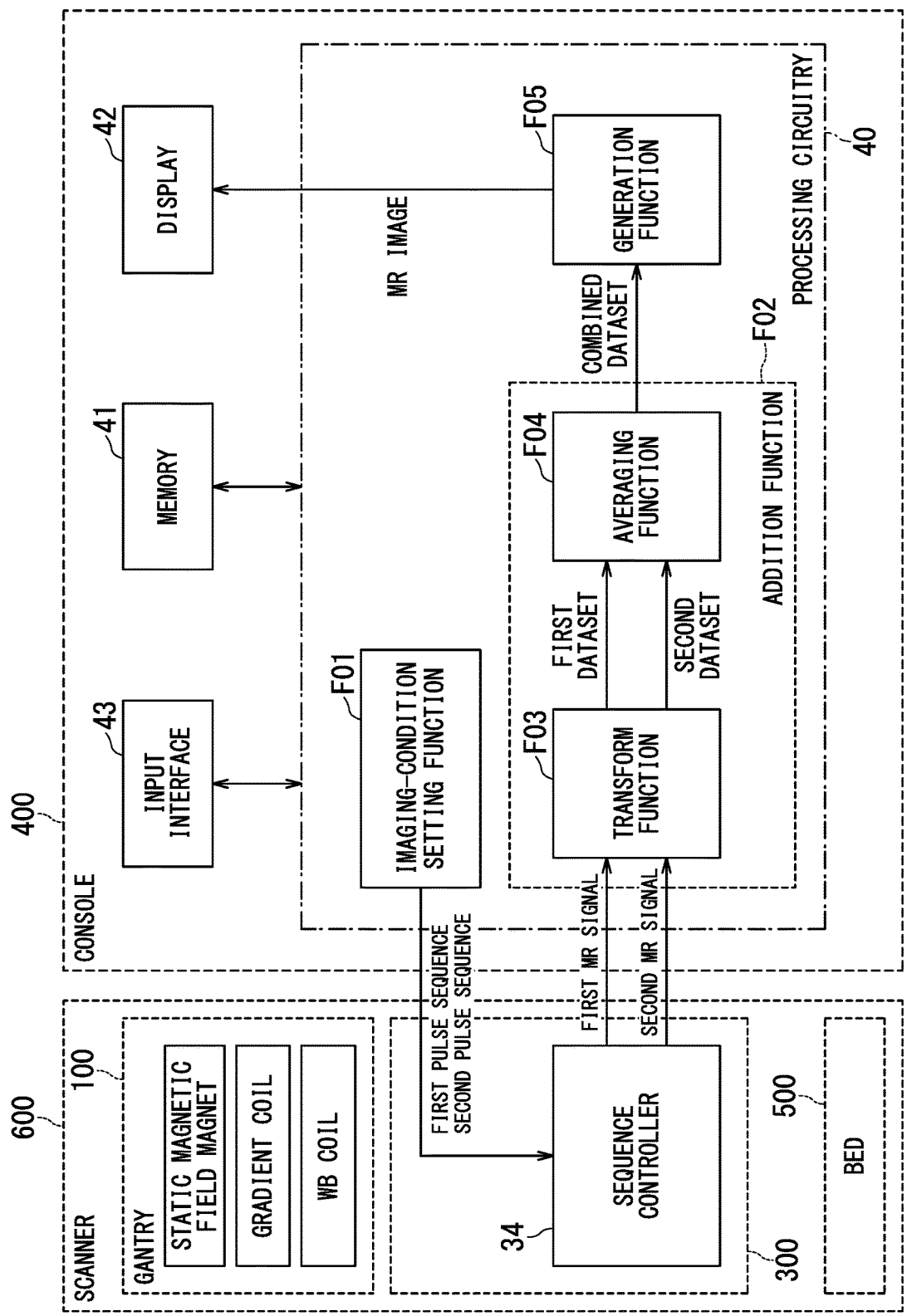
FIG. 6 is a block diagram of the MRI apparatus according to the first embodiment including a configuration for suppressing N/2 artifacts.

FIG. 6 is a block diagram of the MRI apparatus 1 according to the first embodiment including the configuration for suppressing N/2 artifacts. As shown in FIG. 6, the processing circuitry 40 of the MRI apparatus 1 implements each of an imaging-condition setting function F01, an addition function F02, and a generation function F05. The addition function F02 is composed of a transform function F03 and an averaging function F04. Each of these functions is achieved by the processor of the processing circuitry 40 executing predetermined programs, as described above.

Of the configuration of the MRI apparatus 1 shown in FIG. 1, all the components excluding the console 400 (i.e., the gantry 100 including the static magnetic field magnet 10, the control cabinet 300 including the sequence controller 34, and the bed 500) constitute a scanner 600. The memory 41, the input interface 43, and the display 42 in FIG. 6 are the same as those shown in FIG. 1, and are denoted by the same reference signs.

Among the above-described components, the imaging-condition setting function F01 sets a first pulse sequence and a second pulse sequence. The first pulse sequence is a pulse sequence in which acquisition of a first set of MR signals is started after elapse of a first delay time from a first excitation pulse, and is a pulse sequence based on the EPI method, for example. The second pulse sequence is a pulse sequence in which acquisition of a second set of MR signals is started after elapse of a second delay time from a second excitation pulse, and is a pulse sequence based on the EPI method similar to the first pulse sequence, for example. Note that the second delay time is different from the first delay time. Details of the first and second pulse sequences are described below.

The scanner 600 applies the first pulse sequence to the object to acquire the first set of MR signals, and applies the second pulse sequence to the object to acquire the second set of MR signals.

The addition function F02 generates a combined dataset by averaging a first dataset based on the acquired first set of MR signals and a second dataset based on the acquired second set of MR signals. The averaging function F04 included in the addition function F02 performs different averaging in the following three cases.

In the first case, each of the first dataset and the second dataset to be averaged is a dataset defined in the k-space. In this case, the coordinates of the space of each of the first dataset and the second dataset are represented by, for example, (kx, ky). In this case, the transform function F03 sends the digitized first and second sets of MR signals outputted from the sequence controller 34, without performing any change but substantially as they are, as the first and second datasets to the averaging function F04. The averaging function F04 generates the combined dataset by performing complex addition on the first and second datasets defined in the k-space.

The generation function F05 generates (i.e., reconstructs) a magnetic resonance image on the basis of the combined dataset. In the first case, the generated combined dataset is a dataset defined in the k-space. Thus, in the first case, the generation function F05 transforms the combined dataset into a real-space dataset by, for example, two-dimensional Fourier transform so as to generate the magnetic resonance image.

In the second case, each of the first and second datasets to be averaged is a dataset defined in a hybrid space that is a complex of the real space and the k-space. The hybrid space is, for example, a space in which the X-axis direction is defined by the real space and the Y-axis direction is defined by the k-space. In this case, the coordinates of the space of each of the first dataset and the second dataset are represented by (X, ky), for example. In this case, of both digitized datasets outputted from the sequence controller 34 (i.e., the first set of MR signals and the second set of MR signals), the dataset in the X-axis direction may be subjected to one-dimensional Fourier transform by the transform function F03 so as to be transformed into a real-space dataset, while the other dataset in the Y-axis direction may be kept as it is, for example. Then, the averaging function F04 generates the combined dataset by performing complex addition of the first and second datasets defined in the hybrid space.

In the second case, the generated combined dataset is a dataset of the hybrid-space in which the X-axis direction is defined by the real space and the Y-axis direction is defined by the k-space. Thus, in the second case, the generation function F05 applies one-dimensional Fourier transform only to the dataset of the Y-axis direction in the combined dataset so as to generate the magnetic resonance image in which both the X-axis and Y-axis directions are transformed into real-space datasets.

In the third case, each of the first and second datasets to be averaged is a dataset defined in the real space. In this case, the coordinates of the space of each of the first and second datasets are represented by, for example, (X, Y). In this case, the transform function F03 transforms each of the digitized first and second sets of MR signals outputted from the sequence controller 34 into a two-dimensional real-space dataset by, for example, performing two-dimensional Fourier transform on both to generate the first and second datasets. The averaging function F04 may generate the combined dataset by performing complex addition of the first and second datasets defined in the real space or by adding the absolute values of the first and second datasets.

In the third case, the generated combined dataset is a dataset transformed into the real-space dataset in both the X-axis and Y-axis directions. In the third case, the combined dataset is a substantially magnetic resonance image. Thus, the generation function F05 outputs the inputted combined dataset substantially as it is (i.e., without any change) as a magnetic resonance image.

The respective magnetic resonance images generated in the first to third cases are outputted to the display 42 and provided to the user, for example. Additionally or alternatively, these magnetic resonance images may be stored in the memory 41 or in an external image server.

Figure 7:
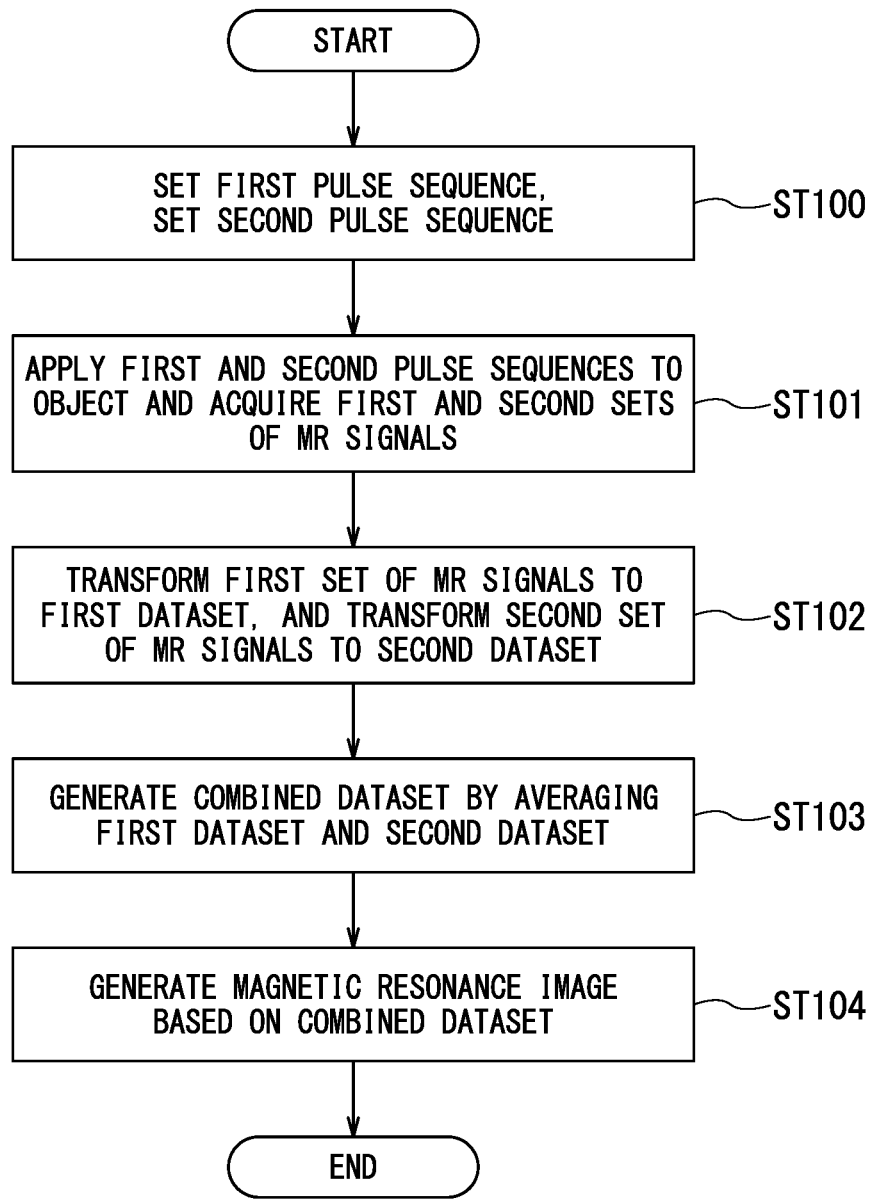
FIG. 7 is a flowchart illustrating the N/2 artifact suppression processing to be executed by the MRI apparatus according to the first embodiment.

FIG. 7 is a flowchart illustrating N/2 artifact suppression processing to be executed by the MRI apparatus 1 according to the first embodiment.

In the first step ST100, the imaging-condition setting function F01 sets the first pulse sequence and the second pulse sequence.

Figure 8A:
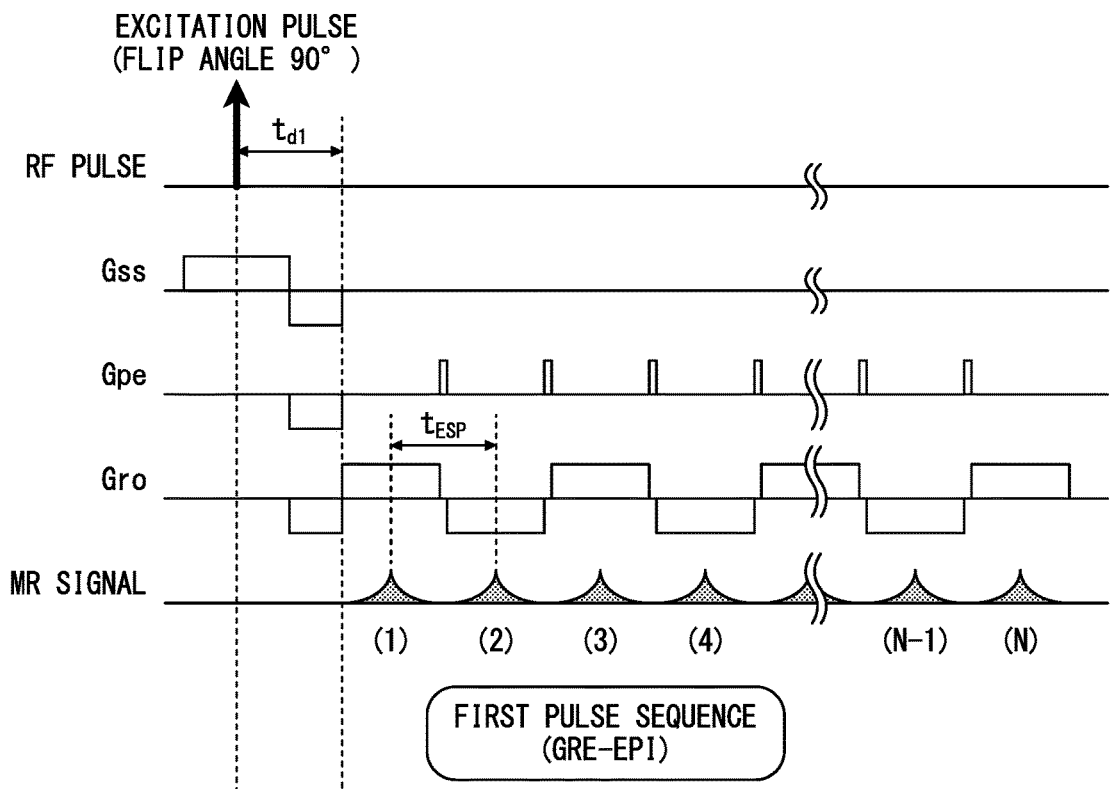
FIG. 8A and FIG. 8B are sequence diagrams illustrating the first aspect of the first and second pulse sequences in the first embodiment.
Figure 8B:
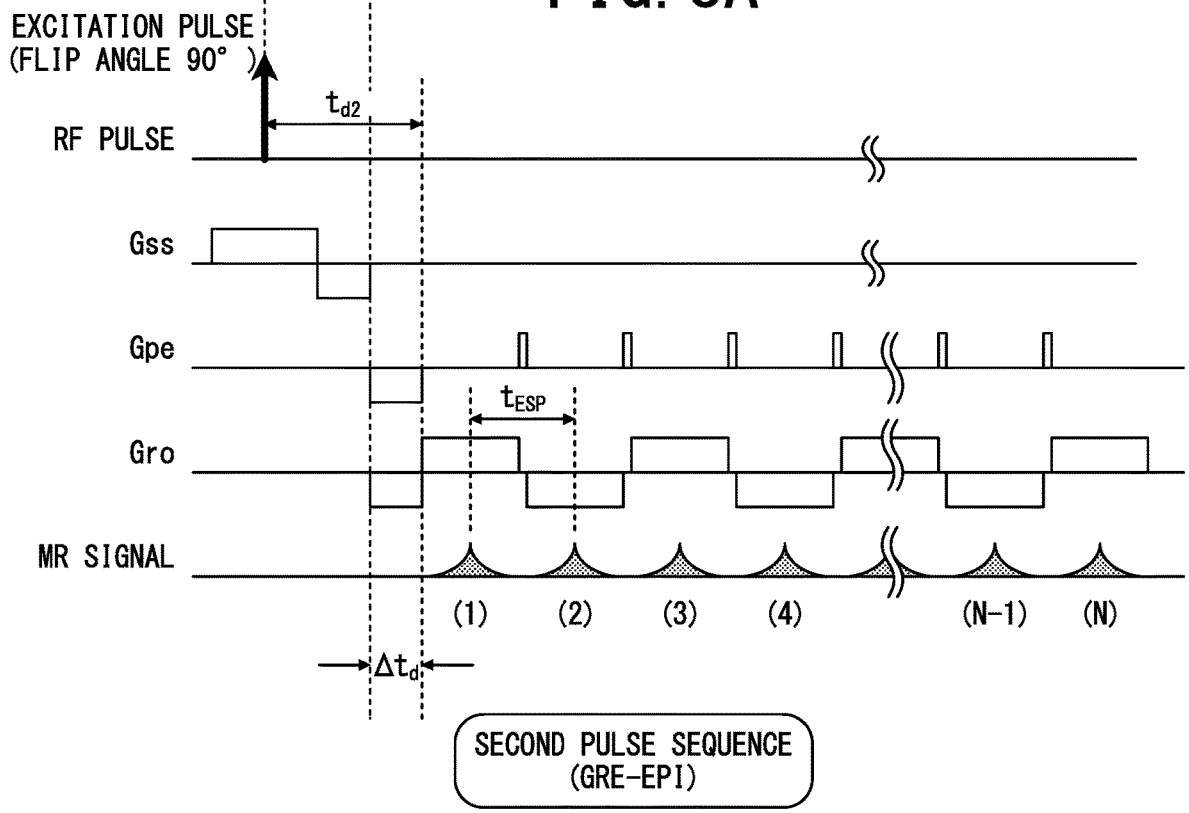

FIG. 8A and FIG. 8B are sequence diagrams illustrating the first aspect of the first and second pulse sequences. As shown in FIG. 8A, in the first pulse sequence, acquisition of the first set of MR signals of numbers (1) to (N) is started after elapse of the first delay time $t_{d1}$ from the application of the excitation pulse (i.e., the first excitation pulse).

As shown in FIG. 8B, in the second pulse sequence, acquisition of the second set of MR signals of numbers (1) to (N) is started after elapse of the second delay time $t_{d2}$ from the application of the excitation pulse (i.e., the second excitation pulse). Note that the second delay time $t_{d2}$ is different from the first delay time $t_{d1}$.

The first and second pulse sequences are, for example, pulse sequences of the GRE-based EPI method (GRE-EPI) shown in FIG. 2A. The first delay time $t_{d1}$ is a time from the application of the first excitation pulse to the readout of the first MR signal by the first readout gradient pulse among the plurality of readout gradient pulses in the EPI method. Similarly, the second delay time $t_{d2}$ is a time from the application of the second excitation pulse to the readout of the first MR signal by the first readout gradient pulse among the plurality of readout gradient pulses in the EPI method.

The difference between the first and second pulse sequences lies in the difference between the first delay time $t_{d1}$ and the second delay time $t_{d2}$. The difference $\Delta t_d$ between the first delay time $t_{d1}$ and the second delay time $t_{d2}$ is desirably set to a small value such that difference between the MR signals acquired by the first and second pulse sequences due to transverse relaxation does not become too large. For example, it is preferred that $\Delta t_d$ is equal to or smaller than ESP. For example, $\Delta t_d$ may be set to approximately ½ of ESP. Note that the ESP (or the $t_{ESP}$) is defined as the interval between adjacent individual readout gradient pulses in the EPI method (i.e., time interval between the adjacent two sets of the MR signal read out by the readout gradient pulse).

Figure 9A:
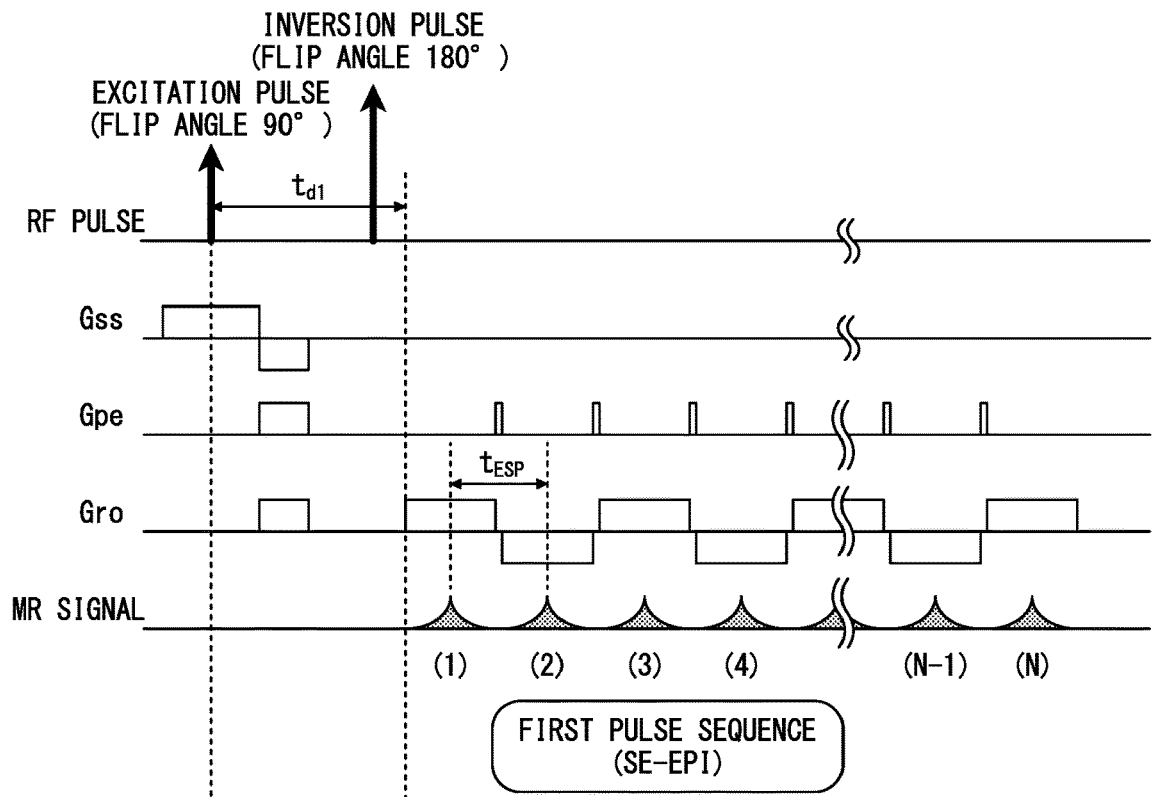
FIG. 9A and FIG. 9B are sequence diagrams illustrating the second aspect of the first and second pulse sequences in the first embodiment.
Figure 9B:
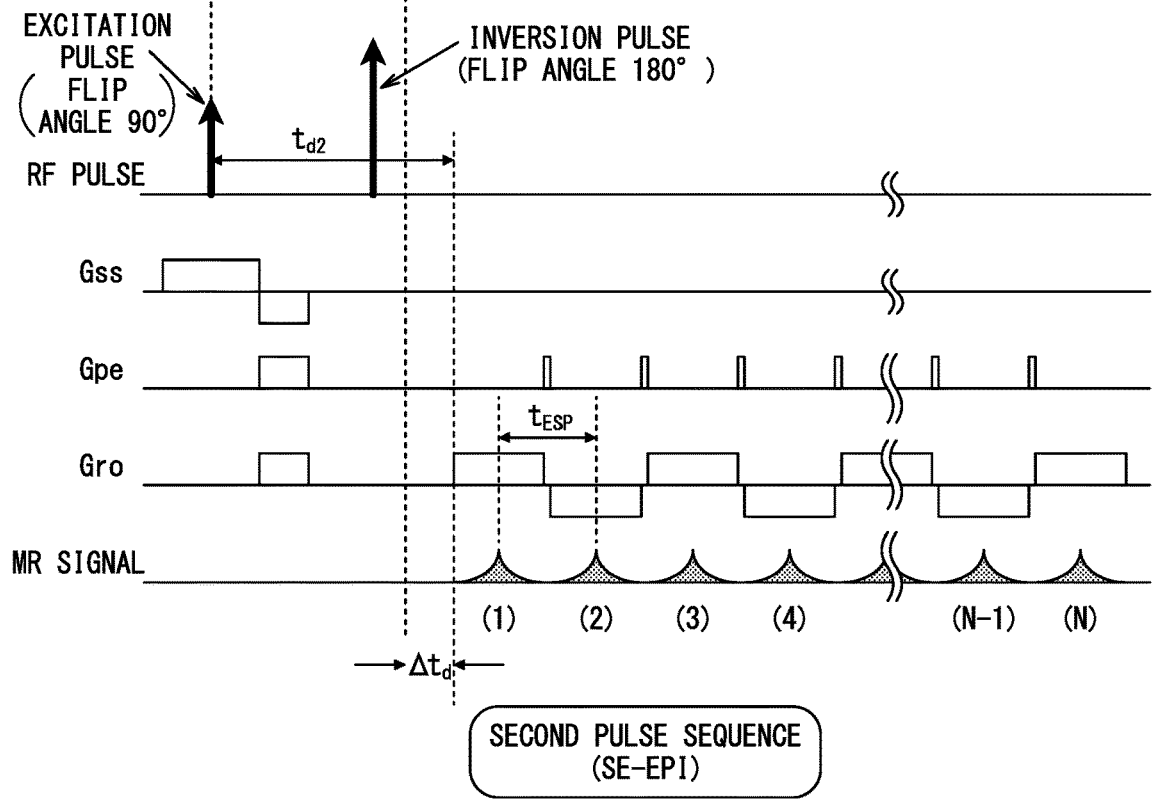

FIG. 9A and FIG. 9B are sequence diagrams illustrating the second aspect of the first and second pulse sequences. The first and second pulse sequences in the second aspect are pulse sequences of a SE (spin echo)-based EPI method (SE-EPI). In the SE-based EPI pulse sequence, an excitation pulse is followed by an inversion pulse with a flip angle of, for example, 180°, and then a set of MR signals of numbers (1) to (N) are acquired in response to application of each readout gradient pulse.

Also in the SE-based EPI pulse sequence, the first pulse sequence (FIG. 9A) starts acquisition of the first set of MR signals after elapse of the first delay time $t_{d1}$ from the application of the excitation pulse (i.e., the first excitation pulse), and the second pulse sequence (FIG. 9B) starts acquisition of the second set of MR signals after elapse of the second delay time $t_{d2}$ from the application of the excitation pulse (i.e., the second excitation pulse). Also in this case, the first delay time $t_{d1}$ is different from second delay time $t_{d2}$.

Similar to the GRE-based EPI, in FIG. 9A and 9B, the first delay time $t_{d1}$ is a time from the application of the first excitation pulse to the readout of the first MR signal by the first readout gradient pulse among the plurality of readout gradient pulses, and the second delay time $t_{d2}$ is a time from the application of the second excitation pulse to the readout of the first MR signal by the first readout gradient pulse among the plurality of readout gradient pulses.

The difference $\Delta t_d$ between the first delay time $t_{d1}$ and the second delay time $t_{d2}$ is preferably equal to or smaller than ESP similarly to the GRE-based EPI, and may be set to approximately ½ of ESP, for example.

Returning to FIG. 7, in the step ST101, the scanner 600 applies the first and second pulse sequences set in the step ST100 to the object to acquire the first set of MR signals and the second set of MR signals.

In the next step ST102, the transform function F03 of the processing circuitry 40 transforms the first and second sets of MR signals into the first and second datasets, respectively.

In the next step ST103, the averaging function F04 of the processing circuitry 40 averages the first and second datasets to generate the combined dataset.

In the next step ST104, the generation function F05 of processing circuitry 40 generates magnetic resonance images based on the combined dataset.

As described above, the processing in the step ST103 includes three cases of: averaging in the k-space; averaging in the hybrid space; and averaging in the real space. Depending on which of these three cases, the processing to be performed by the transform function F03 and the processing to be performed by the generation function F05 are slightly different as described above.

Figure 10:
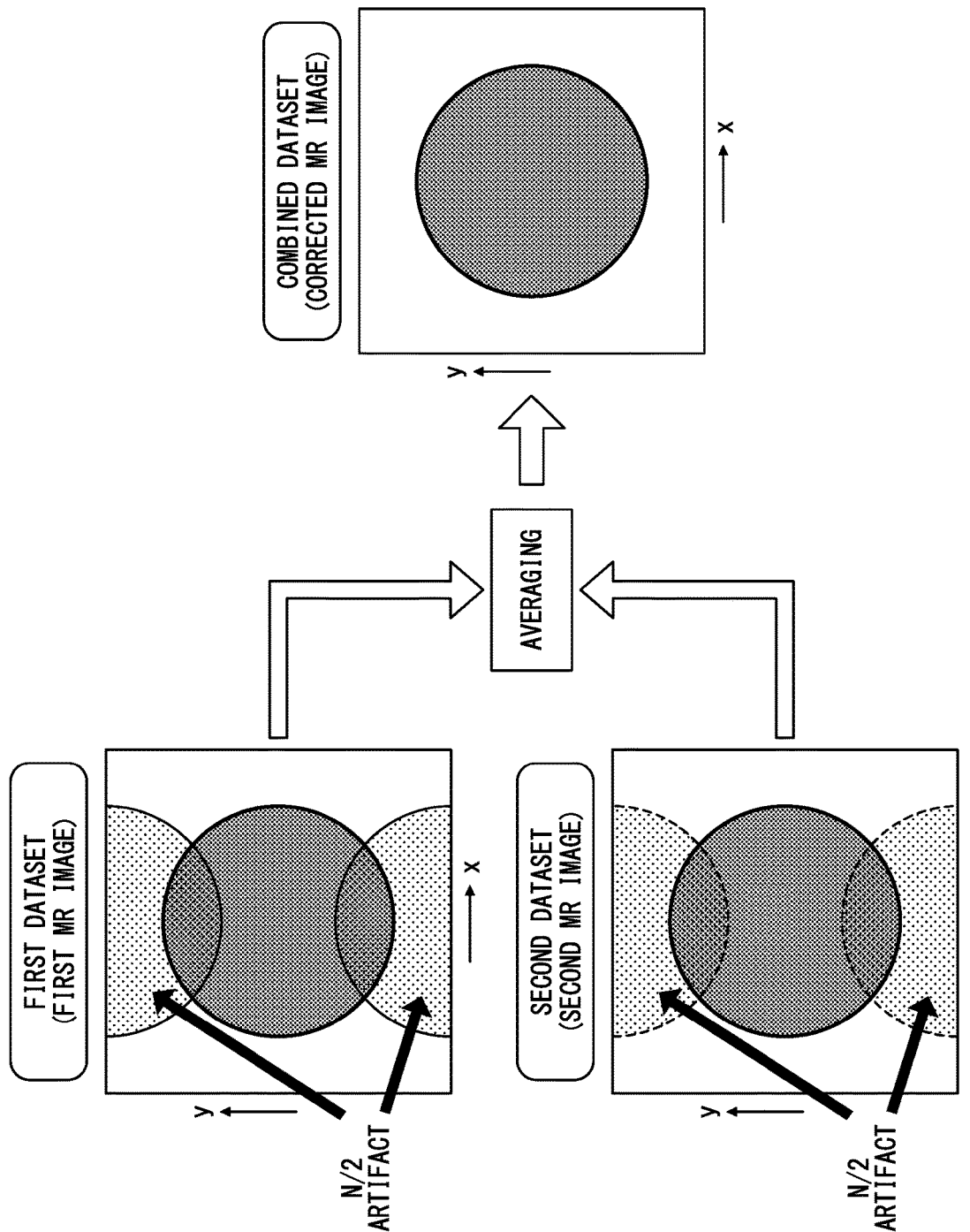
FIG. 10 is a schematic diagram illustrating the effect of the N/2 artifact suppression processing executed by the MRI apparatus according to the first embodiment.

FIG. 10 is a schematic diagram illustrating the effect of the N/2 artifact suppression processing to be executed by the MRI apparatus 1 according to the first embodiment.

FIG. 10 illustrates a case where averaging is performed in the real space. In this case, the first dataset is the first MR image transformed into the real space, and the second dataset is the second MR image transformed into the real space.

As shown in the upper and lower diagrams on the left side of FIG. 10, N/2 artifacts are generated in each of the first MR image and the second MR image.

The common fact between the N/2 artifacts in the first MR image and the N/2 artifacts in the second MR image is that the N/2 artifacts appear at the position where the true image (denoted by the central circle) is shifted exactly by ½ of the FOV in the phase encoding direction. Also, the shape of the N/2 artifacts are common to both the first MR image and the second MR image.

However, the delay time $t_d$ from the application of the excitation pulse to the acquisition of a set of MR signals, from which the MR image is derived, is different between the first MR image and the second MR image. Thus, between the N/2 artifacts in the first MR image and the N/2 artifacts in the second MR image, amplitudes and phases of the corresponding pixel values (i.e., pixel values of pixels at the same position) show values different from each other.

As a result, averaging of the first MR image and the second MR image smooths the pixel values of N/2 artifacts, and N/2 artifacts are reduced as shown in the right part of FIG. 10.

Second Embodiment

Figure 11:
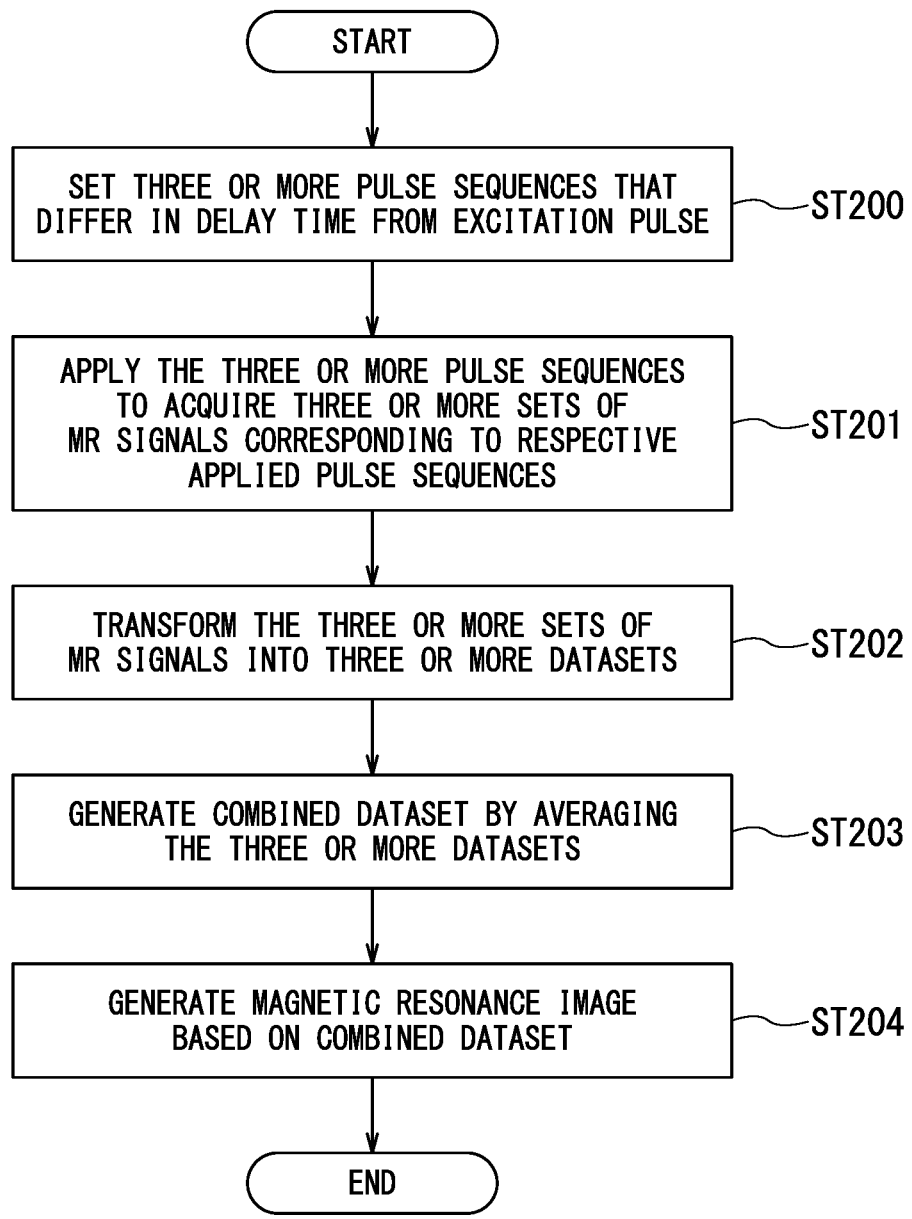
FIG. 11 is a flowchart illustrating the N/2 artifact suppression processing executed by the MRI apparatus according to the second embodiment.

FIG. 11 is a flowchart illustrating the N/2 artifact suppression processing executed by the MRI apparatus 1 according to the second embodiment. The difference between the first and second embodiments lies in the number of data to be averaged, while the MRI apparatus 1 of the second embodiment and the MRI apparatus 1 of the first embodiment shown in FIG. 1 and FIG. 6 have the same configuration.

In the step ST200 of FIG. 11, the imaging-condition setting function F01 sets three or more pulse sequences that are different in delay time from the application of the excitation pulse to the start of acquisition of a set of MR signals.

The plurality of pulse sequences may be pulse sequences of the GRE-based EPI method (GRE-EPI) or pulse sequences of the SE-based EPI method (SE-EPI), similar to the first embodiment.

FIG. 12A to FIG. 12D are sequence diagrams and respectively illustrate the first, second, third, and fourth pulse sequences of the GRE-based EPI method set in the second embodiment. The first pulse sequence (FIG. 12A) to the fourth pulse sequence (FIG. 12D) differ from each other in terms of delay time $t_{dn}$ (n=1 to 4) from the application of the excitation pulse to the readout of the first MR signal by the first readout gradient pulse among the plurality of readout gradient pulses.

It is preferred that the maximum delay time (i.e., delay time $t_{d4}$ in this case) of the plurality of delay times is equal to or smaller than ESP (i.e., $t_{ESP}$ or shorter). The delay time $t_{dn}$ (n=1 to 4) is desirably set in such a manner that each difference $\Delta t_{dm}$ (m=1 to 3) between adjacent delay times becomes a substantially equal value (=$\Delta t_d$) when sorting the delay times $t_{dn}$ (n=1 to 4) of the respective pulse sequences in descending order or ascending order.

Returning to FIG. 11, in the step ST201, the scanner 600 applies the three or more pulse sequences having been set in the step ST200 to the object so as to acquire three or more sets of MR signals corresponding to the respective applied pulse sequences.

In the next step ST202, the transform function F03 of the processing circuitry 40 transforms the three or more sets of MR signals into three or more datasets.

In the next step ST203, the averaging function F04 of the processing circuitry 40 averages the three or more datasets to generate the combined dataset.

In the next step ST204, the generation function F05 of the processing circuitry 40 generates (i.e., reconstructs) magnetic resonance images on the basis of the combined dataset.

Also in the second embodiment, the averaging processing in the step ST203 includes three cases of: averaging in the k-space; averaging in the hybrid space; and averaging in the real space. Same as the first embodiment, the transform function F03 and the generation function F05 perform the processing corresponding to the three cases in the second embodiment.

FIG. 13 is a schematic diagram illustrating the effect of the N/2 artifact suppression processing executed by the MRI apparatus 1 according to the second embodiment.

The first to fourth MR images differ from each other in terms of delay time $t_d$ from the application of the excitation pulse to the acquisition of a set of MR signals, from which the MR image is derived. Thus, between the first MR image to the fourth MR image, the respective N/2 artifacts differ from each other in terms of phase and amplitude of the pixel value of the same position. Hence, when the four MR images (i.e., the first to fourth MR images) are averaged, the pixel values at the common pixel positions in the N/2 artifacts are smoothed in the obtained averaged image, and consequently, the N/2 artifacts are reduced as shown in the lower part of FIG. 13.

Although the second embodiment is longer in imaging time than the first embodiment, the number of datasets to be averaged (for example, the number of MR images) increases in the second embodiment, which enhances the effect of suppressing N/2 artifacts.

Regardless of the number of datasets to be averaged, which is two in the first embodiment and three or more in the second embodiment, it is the same as using the conventional technique that the signal-to-noise ratio of the true image improves as the number of averaging increases. In the above-described first and second embodiments, averaging of two or more datasets enables improvement in signal-to-noise ratio of the true image and suppression of N/2 artifacts at the same time.

It is difficult to suppress N/2 artifacts caused by nonlinear phase errors of second or higher order, by using the first conventional method of suppressing N/2 artifacts. However, by using the N/2 artifact suppression method of each of the first and second embodiments, N/2 artifacts caused by nonlinear phase errors of second or higher order can be suppressed.

The N/2 artifact suppression method of each of the first and second embodiments may be combined with the linear phase correction processing. In this case, the MRI apparatus 1 according to the present embodiment can suppress N/2 artifacts caused by nonlinear phase errors remaining in the case using the first conventional method.

In the second conventional method of suppressing N/2 artifacts, two data acquired by readout gradient pulses of the opposite polarities (i.e., having positive and negative polarities) are added in complex numbers. However, the influence of disturbance caused by, for example, an eddy current differs depending on the polarity of the readout gradient pulse, and thus, there is the problem that complex addition of two MR signals acquired by pulses of the opposite polarities cannot completely eliminate the phase errors. Moreover, due to the opposite polarity of the readout gradient pulse between the main scan and the reference scan, the polarity of the phase error in the readout direction is inverted, and thus, the deviation direction of the positional error in the real space becomes the opposite. Consequently, when two pixel values are added and averaged, an image blur is more likely to occur due to the averaging of the pixel value.

However, in the first and second embodiments, the polarity of the readout gradient pulse is not inverted between a plurality of pulse sequences to be averaged, and thus, the above-described problem in the second conventional method does not occur.

The second conventional method disclosed in Patent Document 2 requires pulse sequences that are opposite to each other in the polarity of the readout gradient pulse, and has a restriction that the number of datasets used for averaging must be an even number.

In the first and second embodiments, there is no such restriction on the number of datasets to be averaged, and the number of datasets to be averaged may be an even number or an odd number.

According to the MRI apparatus of at least one embodiment described above, N/2 artifacts can be reduced by a relatively simple method.

While certain embodiments have been described, these embodiments have been presented by way of example only, and are not intended to limit the scope of the inventions.

Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An MRI apparatus comprising:
   a scanner that includes a static magnetic field magnet configured to generate a static magnetic field, a gradient coil configured to generate a gradient magnetic field, and a whole body (WB) coil configured to apply an RF pulse to an object; and
   processing circuitry configured to
      set a first pulse sequence for performing a first scan and a second pulse sequence for performing a second scan that differs from the first scan,
         the first pulse sequence being a pulse sequence in which acquisition of a first set of MR signals is started after elapse of a first delay time from application of a first excitation pulse,
         the second pulse sequence being a pulse sequence in which acquisition of a second set of MR signals is started after elapse of a second delay time from application of a second excitation pulse, the second delay time being different from the first delay time,
      acquire a first set of MR signals by causing the scanner to apply the first pulse sequence to the object,
      acquire a second set of MR signals by causing the scanner to apply the second pulse sequence to the object,
      generate a combined dataset by averaging a first dataset based on the first set of MR signals and a second dataset based on the second set of MR signals, and
      reconstruct a magnetic resonance image based on the combined dataset.

2. The MRI apparatus according to claim 1, wherein the first pulse sequence and the second pulse sequence are pulse sequences based on an Echo Planar Imaging (EPI) method.

3. The MRI apparatus according to claim 2, wherein:
   the first delay time is a delay time from application of the first excitation pulse to readout of a first MR signal by a first readout gradient pulse among a plurality of readout gradient pulses in the EPI method;
   the second delay time is a delay time from application of the second excitation pulse to readout of a first MR signal by a first readout gradient pulse among a plurality of readout gradient pulses in the EPI method.

4. The MRI apparatus according to claim 2, wherein the processing circuitry is configured to set the first pulse sequence and the second pulse sequence in such a manner that difference between the first delay time and the second delay time is equal to or smaller than an echo space (ESP) which is defined as time interval between adjacent two readout gradient pulses in the EPI method.

5. The MRI apparatus according to claim 2, wherein the processing circuitry is configured to set the first pulse sequence and the second pulse sequence in such a manner that difference between the first delay time and the second delay time becomes substantially half of an echo space (ESP) which is defined as time interval between adjacent two readout gradient pulses in the EPI method.

6. The MRI apparatus according to claim 3, wherein the processing circuitry is configured to set the first pulse sequence and the second pulse sequence in such a manner that difference between the first delay time and the second delay time becomes substantially half of an echo space (ESP) which is defined as time interval between adjacent readout gradient pulses in the EPI method.

7. The MRI apparatus according to claim 1, wherein:
   the first dataset is a dataset in k-space and corresponds to the first set of MR signals;
   the second dataset is a dataset in the k-space and corresponds to the second set of MR signals; and
   the processing circuitry is configured to generate the combined dataset by averaging the first dataset and the second dataset in the k-space.

8. The MRI apparatus according to claim 1, wherein:
   the first dataset is a dataset obtained by transforming the first set of MR signals into a real space;
   the second dataset is a dataset obtained by transforming the second set of MR signals into the real space; and
   the processing circuitry is configured to generate the combined dataset by averaging the first dataset and the second dataset in the real space.

9. The MRI apparatus according to claim 1, wherein:
   the first dataset is a dataset obtained by transforming the first set of MR signals into a hybrid space that is a complex of a k-space and a real space;
   the second dataset is a dataset obtained by transforming the second set of MR signals into the hybrid space; and
   the processing circuitry is configured to generate the combined dataset by averaging the first dataset and the second dataset in the hybrid space.

10. An MRI apparatus comprising:
    a scanner that includes a static magnetic field magnet configured to generate a static magnetic field, a gradient coil configured to generate a gradient magnetic field, and a WB (whole body) coil configured to apply an RF pulse to an object; and
    processing circuitry configured to
       set three or more pulse sequences that differ from each other in delay time from application of an excitation pulse to start of acquisition of a set of MR signals for performing three or more scans; and
       acquire respective three or more sets of MR signals corresponding the three or more pulse sequences by causing the scanner to apply the three or more pulse sequences to the object,
       generate a combined data by averaging three or more datasets based on the respective three or more sets of MR signals, and
       reconstruct a magnetic resonance image based on the combined data.

11. The MRI apparatus according to claim 10, wherein each of the three or more pulse sequences is a pulse sequence based on an EPI (Echo Planar Imaging) method.

12. The MRI apparatus according to claim 11, wherein the processing circuitry is configured to set the three or more pulse sequences in such a manner that:
    a maximum delay time among delay times of the three or more pulse sequences is equal to or shorter than an echo space (ESP), wherein the ESP is defined as time interval between adjacent two readout gradient pulses in the EPI method; and
    each difference in delay time between the three or more pulse sequences becomes substantially equal.

13. A non-transitory computer-readable storage medium storing a program for causing a computer to execute processing comprising:

setting a plurality of pulse sequences that differ from each other in delay time from application of an excitation pulse to start of acquisition of a set of MR signals for performing a plurality of scans;

acquiring respective sets of MR signals corresponding to the plurality of pulse sequences by causing a scanner of an MRI apparatus to apply the plurality of pulse sequences to an object;

generating a combined data by averaging a plurality of datasets based on the respective sets of MR signals; and reconstructing a magnetic resonance image based on the combined data.

\* \* \* \* \*